United States Patent [19]
Gosselin et al.

[11] Patent Number: 5,900,235
[45] Date of Patent: May 4, 1999

[54] INTERLEUKIN-8 AS AN ANTIVIRAL AND ANTITUMOR AGENT

[75] Inventors: Jean Gosselin, Cap-Rouge; Bassam Damaj, Montréal; Pierre Borgeat, Sillery, all of Canada

[73] Assignee: Virocell Inc., Cap-Rouge, Canada

[21] Appl. No.: 08/674,633

[22] Filed: Jul. 5, 1996

[51] Int. Cl.$^6$ .......................... A61K 45/05; A61K 38/00
[52] U.S. Cl. .......................... 424/85.2; 424/85.1; 514/12; 514/13; 514/14; 530/324; 530/325; 530/326; 530/327; 930/141
[58] Field of Search .................. 424/85.1, 85.2; 514/13, 14, 12; 530/324–327; 430/141

[56] References Cited

FOREIGN PATENT DOCUMENTS

WO/96/09062   3/1996   WIPO.

OTHER PUBLICATIONS

Birkenbach, Biosis AB #93:253388, 1993.
Shizawa, Medline AB #91302927, 1991.
Bryson, Medline AB #88116211, 1988.
Andersson, Biosis AB #96:283927, 1996.
Jezek, Biosis AB #96:73089, 1994.
Nakao, Biosis AB #94:230914, 1994.
Hooks, Biosis AB #91:412920.
Klein, Biosis AB #96:563102, 1996.
Wolf, Biosis AB #95:159262, 1995.
Jones, Biosis AB #94:457190, 1994.
Foss, Biosis AB #94:129007, 1994.
Mackewick et al, CD8$^+$ Cell Anti–HIV Activity: Nonlytic Suppression of Virus Replication 1992, vol. 8, No. 6, pp. 1039 to 1050.
Baggiolini, et al, Interleukin–8 and Related Chemotatic Cytokines–CXC and CC Chemokines; 1994, Advances in Immunology, vol. 55, pp. 97 to 179.

*Primary Examiner*—Cecilia J. Tsang
*Attorney, Agent, or Firm*—Swabey Ogilvy Renault; France Côté

[57] ABSTRACT

Interleukin-8 (IL-8) and analogs thereof is useful in the treatment of viral infections, caused by human and animal viruses, and cancers caused by oncoviruses.

15 Claims, 6 Drawing Sheets

INTERLEUKIN-8 AS AN ANTIVIRAL AND ANTITUMOR AGENT

BACKGROUND OF THE INVENTION a) Field of the Invention

The present invention is concerned with antiviral and anticancer activities of interleukin-8 (IL-8) and its use as a therapeutic agent in viral infections caused by human and animal viruses and in cancers caused by oncogene viruses.

b) Description of Prior Art

Many important infectious diseases afflicting mankind are caused by viruses of which some are frequently fatal; among such are rabies, smallpox, poliomyelitis, hepatitis, yellow fever, immune deficiencies and various encephalitic diseases. Others are significant in that they are highly contagious and create acute discomfort such as influenza, measles, mumps and chickenpox, as well as respiratory-gastrointestinal disorders. Others such as rubella and cytomegalovirus can cause congenital abnormalities; finally, there are viruses, known as oncoviruses, that can cause tumors and cancer in humans and animals.

Among viruses, the family of Herpesviridae is of great interest. Herpes viruses are highly disseminated in nature and highly pathogenic for man. For example, Epstein-Barr virus (EBV) is known to cause infectious mononucleosis in late childhood or adolescence or in young adults. The hallmarks of acute infectious mononucleosis are sore throat, fever, headache, lymphadenopathy, enlarged tonsils and atypical, dividing lymphocytes in the peripheral blood. Other manifestations frequently include mild hepatitis, splenomegaly and cerebritis. EBV is also associated with two forms of cancer: Burkitt's lymphoma (BL) and the nasopharyngeal carcinoma (NPC). In endemic areas of equatorial Africa, BL is the most common childhood malignancy, accounting for approximately 80% of cancers in children. While moderately observed in North American Caucasians, NPC is one of the most common cancers in Southern China with age incidence of 25 to 55 years. EBV, like the cytomegalovirus, is also associated with post-transplant lymphoproliferative disease, which is a potentially fatal complication of chronic immunosuppression following solid organ or bone marrow transplantation.

Another herpes virus, namely Herpes Simplex type 1 (HSV-1) is implicated as the etiologic agent of gingivostomatitis. Manifestations are fever, sore throat, and ulcerative and vesicular lesions in the mouth. The most severe clinical state caused by HSV is the primary genital herpetic infection. While HSV-1 can cause genital herpetic infection, HSV-2 is the main virus associated with this disease. This HSV infection is accompanied by vesicles, pustules and ulcers causing lesions on genital parts. A urinary retention syndrome may also be encountered. More than 80% of people are seropositive to HSV-1 or HSV-2 and studies have indicated a frequency of recurrence or viral reactivation as high as 60%. Other diseases are also associated with HSV including skin and eye infections, for example, chorioretinitis or keratoconjunctivitis. Approximately 300,000 cases of HSV infections of the eye are diagnosed yearly in the United States of America.

Human Herpes virus-6 (HHV-6) has a marked tropism for cells of the immune system and therefore, HHV-6 infection may result in alteration of the immune response. It is now clear that HHV-6 is the cause of exanthem subitum as a primary infection in children. Recent studies indicate that a significant proportion of organ transplant recipients who are seropositive before transplantation, demonstrate serologic evidence of reactivation subsequent to immunosuppression. Heterophil-negative mononucleosis-like illness and non-A, non-B hepatitis also have been associated with active HHV-6 infection. HHV-6 has often been isolated from patients with human immunodeficiency virus (HIV-1) infections. The fact that HIV and HHV-6 can reside in the same target cell has led to speculation that HHV-6 infection may act as a cofactor in the progression of HIV-seropositive patients to symptomatic AIDS. Recent studies also suggest that a human herpes virus is closely associated with HIV diseases. In fact, Kaposi sarcoma (KS), a neoplasm occurring mainly in HIV-infected person, was found to have an infectious etiology. While the virus has been named KS-associated herpesvirus, its formal classification is likely to be HHV-8.

In all infectious diseases, the efficacy of therapy often depends on host immune response. This is particularly true for herpes viruses; indeed, the ability of all herpes viruses to establish latent infections results in an extremely high incidence of reactivated infection in immunocompromised patients. In renal transplant recipients, 40% to 70% reactivate latent HSV infections, and 80% to 100% reactivate CMV infections. Such viral reactivations have also been observed in HIV-positive patients (AIDS).

Today, the number of therapeutic agents available for the treatment of viral infections remains relatively limited. For example, four major compounds are mainly used in the treatment of herpes virus infections: idoxuridine, vidarabine, acyclovir and ganciclovir. Their efficacy is limited and they cause many side effects. Allergic effects have been reported in 35% of patients treated with idoxuridine which is used only to treat HSV infection of the eye. The most common side effects of vidarabine are gastrointestinal disturbances (15% of patients). The major side effect of acyclovir is the alteration of renal function; and because acyclovir is a nucleoside analog that can be incorporated in both viral and the host cell DNA, normal division of the host cell can be affected. Regarding ganciclovir, the most important side effects are neutropenia and thrombocytopenia that occur in about 40% of AIDS patients.

Thus, there is an urgent need for the development of efficacious therapy for the treatment of viral infections.

The accumulation of leukocytes in diseased tissues is recognized as a hallmark of the inflammatory process. Recruitment of leukocytes at inflammatory sites is triggered by the local production of chemotactic cytokines. Proteins that exhibit such properties have been classified in two subfamilies according to the position of the first two cysteines, which either are separated by one amino acid (CXC proteins) or are adjacent (CC proteins). The members of the two subfamilies differ in their target cell selectivity and the chromosomal location of their genes (review by Baggiolini, et al., Adv. Immunol. 55: 97, 1994). Among the chemotactic cytokines, interleukin-8 (IL-8), which belongs to the CXC family, was originally identified in the culture supernatants of stimulated human blood monocytes. IL-8 is a nonglycosylated protein synthesized as a precursor of 99 amino acids and secreted after cleavage of a sequence of 20 residues. The mature molecule formed has 79 residues and is processed proteolytically at the N-terminus, yielding the predominant form of 72 amino acids with a molecular weight of about 8383. Structure, sequence and biological properties of IL-8 have been reviewed by Baggiolini M. et al. (Adv. Immunol. 55: 97, 1994).

IL-8 is produced by many cells such as keratinocytes, epithelial cells, synoviocytes and hepatocytes, to name a few. Among peripheral blood leukocytes, monocytes and neutrophils rather than lymphocytes were found to be the major cellular sources of IL-8.

IL-8 exerts many biological activities in vitro and in vivo. IL-8 is well known for its chemotactic activity and its ability to cause degranulation of human neutrophils. Shape change, activation of the motile system and a rise in cytosolic free $Ca^{2+}$ are rapidly detected in neutrophils treated with IL-8. The release of vitamin $B_{12}$-binding protein from specific granules was also observed. IL-8 also causes degranulation of the azurophil granules and release of elastase and other hydrolases. Such degranulation is accompanied by the upregulation of a variety of adhesion molecules at the cell membrane. Degranulation also results in the enhanced expression of the complement receptor type I (CR1) and III (CR3). IL-8 is also a chemotactic factor for eosinophils and for human lymphocytes, particularly T cells.

The biological effects of IL-8 are mediated through seven transmembrane domain, G-protein-coupled receptors. Two types of IL-8 receptors have been described and are defined as the type A and type B. IL-8 receptor type A has a high affinity for IL-8 and a low affinity for Groα(melanoma growth stimulating activity), whereas type B has high affinity for both cytokines. While among peripheral blood leukocytes, neutrophils strongly express both types of IL-8 receptors, monocytes and $CD8^+$ T lymphocytes expressed IL-8 receptors to a lower level. No detectable level of IL-8 receptors was found on B cells and $CD4^+$ T lymphocytes.

There is accumulating evidence in support that IL-8 plays an important role in the inflammatory process of many pathologies; indeed, IL-8 has been detected in inflammatory tissues or exudates such as in psoriatic scale extracts, in synovial fluid from patients with rheumatoid arthritis or gout, in pleural fluid from emphysema patients, and in bronchoalveolar lavages from patients with respiratory distress syndrome. Moreover, antiviral properties have recently been ascribed to the chemokines RANTES and MIP-1α and β, belonging to the C—C chemokine subfamily, which were found to induce inhibition of HIV-1, HIV-2 and SIV replication in vitro Furthermore, IL-8 has been recently reported to have an antiviral effect (Mackewicz and Levy, 1992 AIDS Research and Human Retrovirus 8: 1039–1050). It was shown that IL-8 can inhibit HIV replication in CD4+ lymphocytes under specific conditions. In fact, IL-8 was found to affect viral replication of naturally infected CD4+ cells but had no effect on acutely infected cells. There are several putative mechanisms of antiviral activity; some may be highly selective as sould be the blockade of the attachment of a specific virus to its target cell. Indeed, Idoxuridine, Vidarabine, Acyclovir and Gangiclovir which are specifically used in the treatment of Herpes virus infection, have no effect on other viruses such as HIV, and thus constitute examples of drugs with selective antiviral activity.

Accordingly, data presented by Mackowicz and Levy in no way make predictable that IL-8 might show antiviral activity against all viruses. The selectivity for specific viruses of most drugs presently used in the treatment of viral infection strongly supports this statement. Therefore, the report of the antiviral effect of IL-8 on HIV does not allow any conclusion on the general antiviral activity of IL-8. To date, there is no other proven report of antiviral activity of IL-8.

Finally, TALMADGE'S PCT application PCT/US95/12099 published Mar. 28, 1996 under the publication number WO 96/09062 describes polypeptide analogs of IL-8 and claims that the analogs can be used for the treatment of pathological conditions such as viral infection, bacterial infection, fungal infections, yeast infection, parasitic infection among others. However, TALMADGE doe not present any data to prove its claim which is based on extrapolation or mere desire for the polypeptide to do so.

It would be highly desirable to provide an antiviral agent with greater efficacy and which would not present the undesirable side effects of the known antiviral agents.

SUMMARY OF THE INVENTION

The present invention provides methods for the prophylaxis or treatment of viral infections and cancer caused by oncoviruses.

In accordance with these methods, a pharmaceutically or physiologically acceptable, therapeutically effective amount of an interleukin-8 agent is administered to a human or animal in need of such treatment.

One aim of the present invention is to provide an antiviral agent and method which would be more efficacious for the prophylaxis and treatment of viral infections and which would not present the undesirable side effects of the known antiviral agents.

Another aim of the present invention is to provide an antiviral agent and method for the prophylaxis or treatment of cancers induced by oncoviruses such as retroviruses, papillomaviruses, adenoviruses and herpesviruses.

Another aim of the present invention is to provide an antiviral agent and method for the prophylaxis or treatment of viral infections in immunosuppressed patients and animals.

In accordance with the present invention, there is provided the use of IL-8 agent as an antiviral agent against herpes viruses selected from the group consisting of EBV, HSV-1, HSV-2, CMV, VZV, HHV-6, HHV-7 and HHV-8; and in a method for the prophylaxis or treatment of infections caused by such herpes viruses.

In accordance with the present invention, there is also provided the use of IL-8 agent as an antiviral agent against other human and animal viruses, including, but not limited to, porcine enteroviruses belonging to the picornaviridae or bovine diarrhea virus belonging to the togaviridae family, or bovine respiratory syncytial virus belonging to the paramyxoviridae.

In accordance with the present invention, there is also provided the use of IL-8 agent as an antiviral agent in the treatment of viral infections in humans and animals in association with other antiviral agents, including but not limited to interferon-α, -β, -γ, tumor necrosis factor α, ganciclovir, acyclovir, vidarabine, idoxuridine, and prostaglandins or prostaglandin analogs.

In accordance with the present invention, there is also provided the use of IL-8 agent as an antiviral agent for the prophylaxis and treatment of cancers induced by oncoviruses such as retroviruses, papillomaviruses, adenoviruses and herpesviruses.

In accordance with the present invention, there is also provided the use of IL-8 agent as an antiviral agent against cancers induced by oncoviruses in association with other anticancer agents including but not limited to adriamycine, cyclophosphamide and methotrexate.

In accordance with the present invention, there is also provided the use of IL-8 agent as an antiviral agent for the prophylaxis and treatment of viral infections in immunosuppressed patients and animals.

Immunosuppressed patients include patients who have undergone organ or tissue transplantation and are treated with immunosuppressive agents including but not limited to azathioprine, corticosteroids, adriamycine, cyclophosphamide and methotrexate. Immunosuppressed patients also include patients with any form of cancer or neoplasic diseases treated or not with anticancer chemotherapeutic agents including but not limited to adriamycine, cyclophosphamide and methotrexate. Immunosuppressed patients also include patients with inflammatory diseases treated with antiinflammatory agents including but not limited to corticosteroids, methotrexate, azathioprine and cyclophosphamide. Immunosuppressed patients also include patients with shock or severe trauma including but not limited to burn injury, or patients undergoing chronic hemodialysis.

In accordance with the present invention, there is also provided the use of IL-8 agent as an antiviral agent against viral infections in immunosuppressed patients and animals in association with other antiviral agents.

BRIEF DESCRIPTION OF THE DRAWINGS

The file of this patent contains at least one drawing executed in color: Copies of this patent with color drawing(s) will be provided by the Patent Trademark Office upon request and payment of the necessary fee.

Figure 1A:
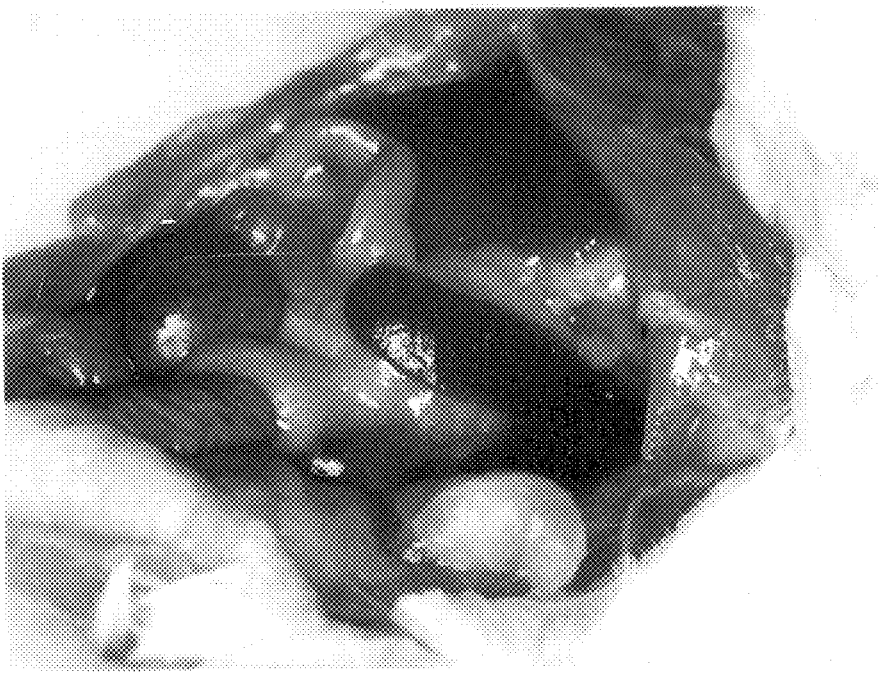
FIGS. 1a to 1f illustrate the inhibitory effect of IL-8 on EBV-induced tumor growth and splenomegaly in SCID mice.

DESCRIPTION OF PREFERRED EMBODIMENTS WITH REFERENCE TO THE DRAWINGS i) IL-8 Agent The IL-8 agent of the present invention is interleukin-8 in the 72 amino acid form or the 77 amino acid form, derivatives or analogs of interleukin-8. It is known in the art that minor addition or deletion of amino acids to IL-8 may slightly alter, viz. enhancing or decreasing the activity of IL-8. Accordingly, derivatives and analogs of IL-8 also includes modified peptides showing significant biological activity analogous to that of IL-8 in various biological systems. Significant biological activity in the context of the invention includes but is not limited to the activation of human neutrophils and thus also includes an antiviral activity similar to that of IL-8.

The term IL-8 agent also includes antibodies to the IL-8 receptor, or anti-idiotypic antibodies to antibodies raised against IL-8 or one of the above-mentioned analogs or variants of IL-8, which elicit an IL-8-like biological response, such as an antiviral effect.

The term IL-8 agent also includes the IL-8 receptors (types A and B) or other receptors which bind IL-8, or peptides corresponding to selected regions of these receptors or proteins (or glycoproteins or lipoproteins) of the viral envelope or peptides corresponding to selected regions of these proteins, which prevent the binding of viral particles to the IL-8 receptors or to other receptors which bind IL-8.

The term IL-8 agent also includes analogs or variants of the IL-8 receptors (or of other receptors which bind IL-8); analogs or variants of peptides corresponding to selected regions of these receptors; and proteins (or glycoproteins or lipoproteins) of the viral envelope, of peptides corresponding to selected regions of these proteins.

The term IL-8 agent however does not include peptides of about 17 amino acids having the following formula:

Glu-Leu-Arg-Cys-Xaa$_1$-Cys Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$ wherein:

Xaa$_1$ is Gln, Met, or Val;
Xaa$_2$ is Ile, or Val;
Xaa$_3$ is Lys, Gln, or Ser;
Xaa$_4$ is Thr, or Ile;
Xaa$_5$ is Tyr, Leu, Met, His, Val, or Thr;
Xaa$_6$ is Ser, Gln, Thr, or Ala;
Xaa$_7$ is Lys, Arg, or His;
Xaa$_8$ is absent or is Pro, Phe, or Gly;
Xaa$_9$ is absent or is Phe, Ile, or Val;
Xaa$_{10}$ is absent or is His, Lys, or Arg;
Xaa$_{11}$ is absent or is Pro, Leu, or Phe; and
Xaa$_{12}$ is absent or is Lys, His or Arg.

ii) Viral infections

The viral infections which may be treated with the IL-8 agent, in accordance with the invention, are infections caused by human and animal viruses.

The expression "human and animal viruses" is intended to include, without limitation, DNA and RNA viruses in general and Retroviridae. DNA viruses include parvoviridae, papovaviridae, adenoviridae, herpesviridae, poxviridae and hepadnaviridae. RNA viruses include picornaviridae, togaviridae, orthomyxoviridae, paramyxoviridae, coronaviridae, reoviridae, oncornaviridae and filoviridae.

The antiviral activity of IL-8 against the Epstein-Barr virus (EBV) has been investigated in vivo. It is well-known that SCID mice, characterized by the absence of B and T lymphocytes, often develop B lymphomas when reconstituted with peripheral blood lymphocytes from EBV-infected donors. This infection is accompanied by splenomegaly, enlargement of the peritoneal cavity and diarrhea. Thus, SCID mice represent an interesting in vivo model of human lymphomagenesis involving viral pathogens. To evaluate the antiviral activities of IL-8, EBV-transformed B cells (B95-8 cell line) were injected intraperitoneally into SCID mice; IL-8 was then administered intraperitoneally in different schedules in accordance with Table 1 below.

TABLE 1

Protocol of the in vivo study of the effects of IL-8 on EBV-infected SCID mice

| | |
|---|---|
| Group 1 | Untreated, animals |
| Group 2 | Injection of IL-8 on day 0 |
| Group 3 | Injection of B95-8 cells on day 0 |
| Group 4 | Injection of B95-8 cells and of IL-8 on day 0 at 30 min interval |
| Group 5 | Injection of B95-8 cells on day 0 and of IL-8 on days 0, 1, 2, 3, 4, 5 |
| Group 6 | Injection of B95-8 cells on day 0 and of IL-8 on days 0, 7, 15, 21, 28 |
| Groups 1–6 | Animals sacrificed and autopsied at day 49 |

EBV-infected B95-8 cells (60 × 10$^6$) were injected intraperitoneally (IP) into SCID mice. At the indicated times, mice were treated with recombinant IL-8. After 49 days, mice were sacrificed and autopsied. Each group consisted of 3 mice. IL-8 was always administered as a 25 µg bolus (IP) per mouse, in solution in NaCl 0.9% containing 0.01% BSA.

At four weeks post-infection, mice treated with B95-8 cells alone showed a significant inflammation of the peritoneal cavity as assessed by the occurrence of abdominal swelling, and had diarrhea, a characteristic of tumor growth in this model. In contrast, such symptoms were not observed in mice treated 5 times with 25 µg of IL-8 at one week intervals (group 6).

In mice treated with 25 µg IL-8 for 6 consecutive days (group 5), the diarrhea was observed at four weeks post infection but was less severe than in infected untreated animals (group 3).

In mice treated only once with 25 µg IL-8 (group 2), the peritoneal inflammation and diarrhea observed at four weeks post infection was as severe as in infected untreated animals of group 3.

At four weeks, animals of groups 1, 2 and 6 appeared normal and did not show the above-mentioned symptoms. Animals of group 3 died in the course of the $5^{th}$ and $6^{th}$ weeks post infection; autopsy revealed massive hemorrhage at the level of spleen and liver. At seven weeks post infection, surviving animals of all groups were sacrificed and autopsied.

Figure 1B:

Infected animals treated once with IL-8 (group 4) showed marked splenomegaly and a tumor of approximately 0.7 cm diameter was found in each mouse, as shown in FIG. 1b. In non-infected, untreated animals (group 1), spleens were normal and the tumor was absent as shown in FIG. 1a. In animals treated six consecutive days with 25 µg IL-8 (group 5), splenomegaly and the tumor were observed but were reduced in comparison to animals of group 4. In animals treated four times with 25 µg IL-8 at one week intervals (group 6), tumors were not detectable and spleens (and other organs) were morphologically undistinguishable from those of uninfected animals (groups 1 and 2).

Figure 2A:
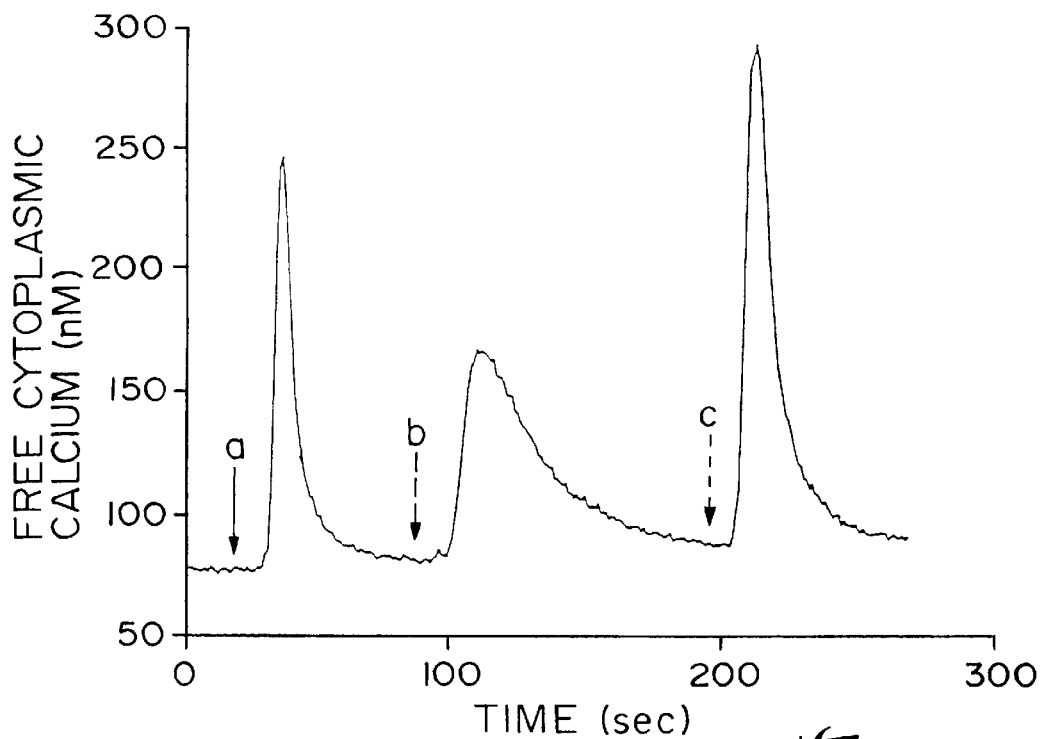
FIGS. 2a, 2b and 2c illustrate the effects of IL-8 and Gro$\alpha$on EBV-induced Ca$^{2+}$ mobilization in human neutrophils.
Figure 2B:
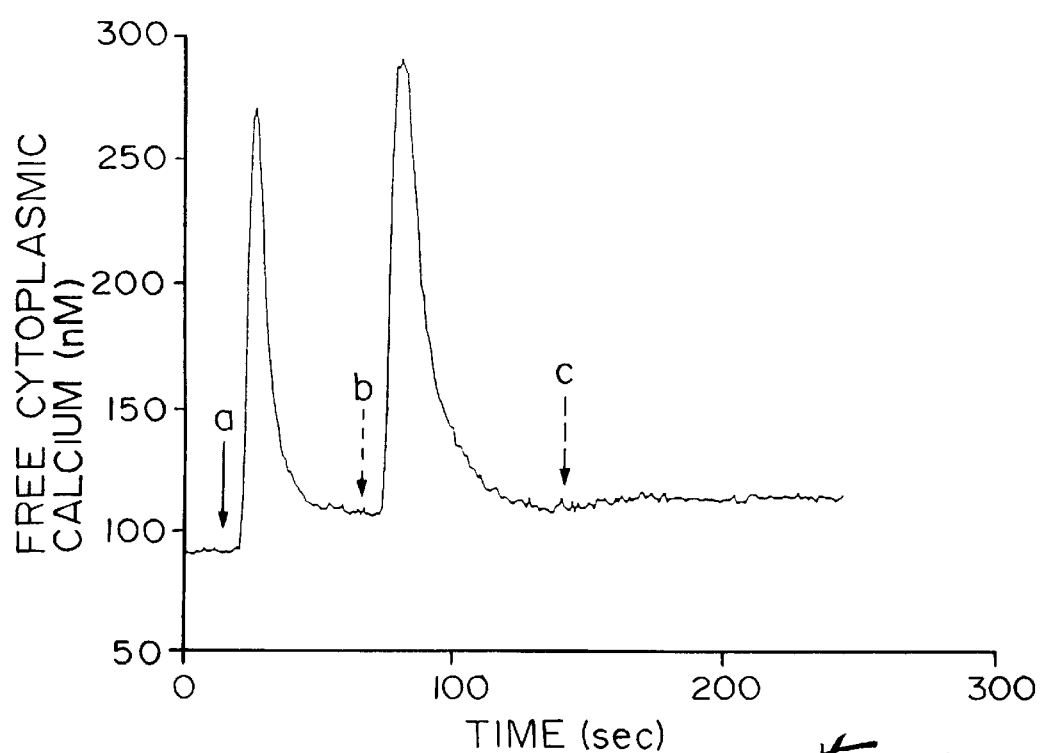
Figure 2C:
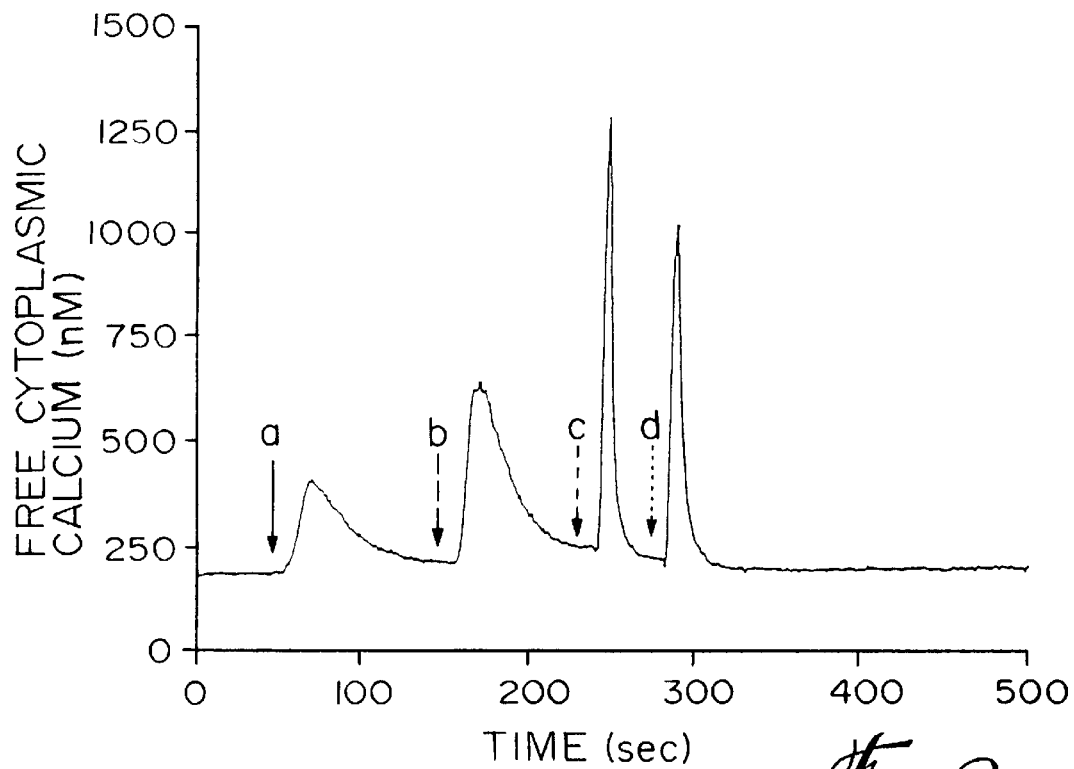

EBV has recently been shown to interact with human neutrophils in vitro and to modulate RNA and protein synthesis. IL-8 is known to induce shape change and a transient rise of the intracellular free $Ca^{2+0}$ concentration ($[Ca^{2+}]i$) in human neutrophils. We have observed that EBV induces a similar but not identical (different kinetic of $Ca^{2+}$ accumulation) effect on $[Ca^{2+}]i$ in isolated human neutrophils. We thus investigated the effect of IL-8 on EBV-induced rise in $[Ca^{2+}]i$ in neutrophils. $Ca^{2+}$ mobilization was monitored in human neutrophils loaded with the fluorescent probe FURA-2/AM and treated with IL-8 or Groα prior to or after exposure to EBV. The rise of $[Ca^{2+}]i$ induced by EBV was strongly inhibited when neutrophils were pretreated with IL-8. On the other hand, EBV pretreatment of neutrophils did not suppress the effect of IL-8 or Groα (FIG. 2a, 2b, 2c). Since the IL-8 receptor is a G-protein-coupled receptor, the inventors next examined the potential involvement of G-protein in EBV-induced $Ca^{2+}$ mobilization and RNA synthesis by pretreating neutrophils with pertussis toxin, a known inhibitor of guanine nucleotide-binding regulatory proteins. The results obtained show that pertussis toxin significantly inhibits $Ca^{2+}$ mobilization and RNA synthesis induced by EBV, suggesting that the EBV-induced events are G-protein-mediated.

Figure 3A:
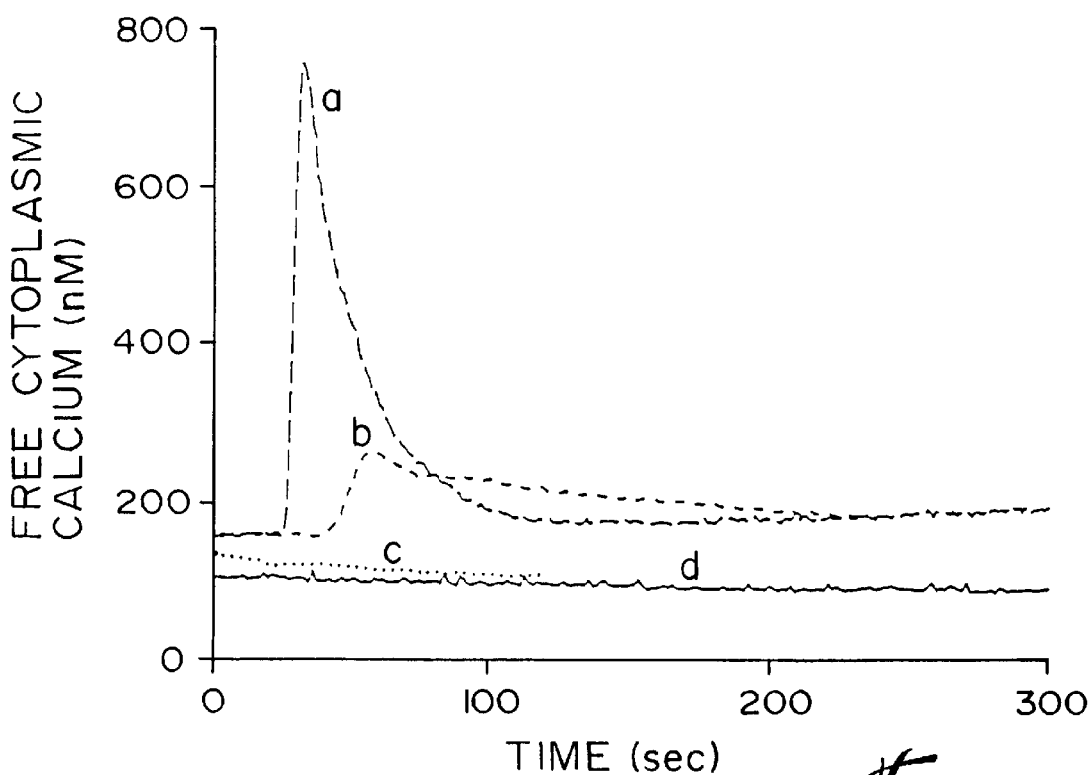
FIGS. 3a and 3b illustrate the effects of pertussis toxin on EBV-induced Ca$^{2+}$ mobilization (A) and RNA synthesis (B) in human neutrophils.

While the mechanism involved in the antiviral and/or antitumoral effect of IL-8 is not clear, it can be hypothesized that IL-8 triggers or amplifies natural antiviral mechanisms, such as the production of tumor necrosis factor alpha (TNFα) or interferons. Alternatively IL-8 might block the putative inhibition of natural antiviral mechanisms induced by EBV. Furthermore, given the observed effect of IL-8 on EBV-induced biological effects on isolated neutrophils (FIGS. 2 and 3), it is also possible that EBV interaction with its target cells involves an IL-8 receptor (or binding sites that can recognize IL-8), in which case IL-8 might prevent the virus-target cell interaction either through competition for the binding site (steric hindrance) or downregulation of receptor expression. Alternatively, exposure of target cells to IL-8 might downregulate receptor functionality through uncoupling of the virus receptor from signal transduction mechanism involved in the process of viral infection including attachment, internalization, replication and downregulation of natural cellular antiviral mechanisms. Additional support for such hypothesis comes from the recent report that chemokine receptor-related proteins are encoded by various viruses and expressed on plasma membrane of infected cells. In the EBV system, it is known that the virus induces BLR-1 (probably identical to EBI-2) and BLR-2 (identical to EBI-1) receptors in transformed cells, which are G-protein-coupled receptors highly homologous to the IL-8 receptor. The expression of these cytokine receptors homologous to IL-8 receptors on EBV-infected cells may render the infected cells, the B cells which do not carry IL-8 receptors, susceptible to a putative antiviral activity of IL-8. These hypotheses are given for the purpose of providing some insights on putative mechanism(s) of the antiviral activity of IL-8 and should not limit the scope of the invention.

These results indicate that IL-8 can be useful in the treatment of viral infections and cancers caused by oncogene viruses.

iii) Dose Ranges

The magnitude of therapeutic dose of an interleukin-8 agent will vary with the nature or the severity of the condition to be treated, with the particular IL-8 agent, with the concommitant use of other active compounds and its route of administration and will be determined based on clinical judgement. It will also vary according to the age, weight and response of the individual patient. An effective dosage amount of the IL-8 agent can thus be determined by pharmacokinetic studies by the clinician after a consideration of all the criteria and use of best judgment on the patient's behalf. In a general manner, the effective dosage is of about 1 to 10 nM in the blood. Accordingly, the clinician will administer a dosage that will produce such concentration in the blood.

iv) Pharmaceutical Compositions

Any suitable route of administration may be employed for providing a mammal, especially a human with an effective dosage of an IL-8 agent of the present invention. For example, the dosage may be administered orally, parenterally, topically, intraarterially, intraperitoneally, intraveneously, intrapleurally, intraoccularly, by injection, subcutaneously or the like. It is understood that injection comprises also perfusion and continuous infusion. Dosage forms include tablets, capsules, powders, solutions, dispersions, suspensions, crams, ointments and aerosols.

The pharmaceutical compositions of the present invention comprise an IL-8 agent as an active ingredient, and a pharmaceutically acceptable carrier and optionally other therapeutic ingredients.

The compositions include compositions suitable for oral or parenteral administration. Conveniently they are presented in unit dosage form and prepared by any of the methods well-known in the art of pharmacy. The unit dosage form may be a slow released unit dosage form.

In practical use, the IL-8 agent can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form in which case solid pharmaceutical carriers are employed. If desired, tablets may be coated by standard aqueous or nonaqueous techniques.

Pharmaceutical compositions of the present invention suitable for oral administration may be presented as discrete units such as capsules, cachets or tablets each containing a predetermined amount of the IL-8 agent, as a powder or granules or as a solution or a suspension in an aqueous liquid, a non-aqueous liquid, an oil-in-water emulsion or a water-in-oil emulsion. Such compositions may be prepared by any of the methods of pharmacy such methods including the step of bringing the IL-8 agent into association with the carrier which includes one or more necessary ingredients. In general, the compositions are prepared by uniformly and intimately admixing the IL-8 agent with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent.

It will be understood that the interleukin-8 agent is to be administered in pharmacologically or physiologically acceptable amounts, by which is to be understood amounts not harmful to the patient, or amounts where any harmful side effects in individual patients are outweighed by the benefits. Similarly, the interleukin-8 agent is to be administered in a therapeutically effective amount, which is to be understood is an amount meeting the intended therapeutic objectives, and providing the benefits available from administration of interleukin-8 agent.

EXAMPLES

In Vivo Studies

Example 1 Antiviral effect of IL-8 on EBV-infected SCID mice in vivo.

Figure 1C:
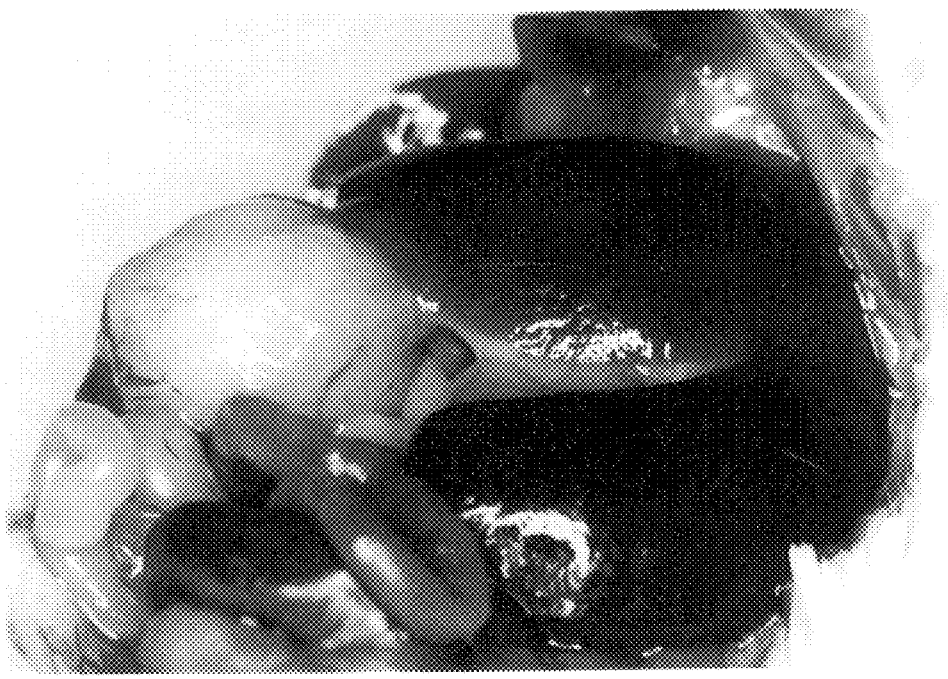
Figure 1D:
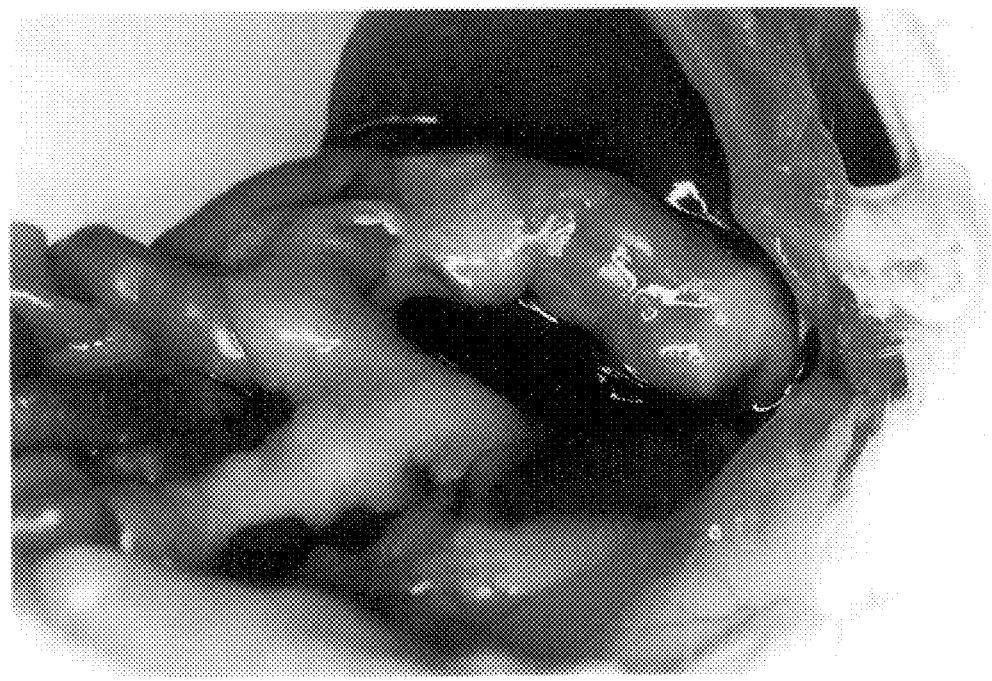
Figure 1E:
Figure 1F:

Female SCID-CB17 mice (Charles River, St. Constant, Canada) aged 8 weeks were used in this study. Six groups of three mice each were formed, infected with EBV-transformed cells and treated or not with IL-8, as summarized in Table 1 above (groups 3 to 6). At day 0, B95-8 cells ($60 \times 10^6$) were injected intraperitoneally (IP) into SCID mice. When indicated, mice also received one or more injections (IP) of IL-8 (groups 2, 4 to 6) (25 μg/mouse/injection) (Peprotech Inc., Rocky Hid, N.J.). The IL-8 used was the 72 amino acid form and was used in solution in NaCl 0.9% containing 0.01% BSA. After seven weeks of treatment, mice were killed by cervical dislocation and autopsied. Tumors and other tissues of interest were photographed (FIGS. 1a to 1f), dissected and kept frozen for immunofluorescence studies and for viral DNA analysis. FIG. 1a illustrates non infected untreated mice (group 1). FIGS. 1b and 1c illustrate EBV-infected mice treated with one injection of IL-8 30 min after infection with B95-8 cells (group 4). FIGS. 1B and 1C show the abdominal cavity of the same animal, FIG. 1C being a close-up photography (group 4). FIGS. 1d and 1e illustrate EBV-infected mice treated weekly with IL-8 during four successive weeks beginning 30 min after infection with B95-8 cells (group 6). FIG. 1f illustrates abdominal cavity of EBV-infected mice treated once with IL-8 (left), four times with IL-8 (middle) and untreated (right).

In Vitro Studies

Example 2
Inhibitory Effect of IL-8 (and Groα) on Calcium Mobilization Induced by EBV in Isolated Human Neutrophils Neutrophil suspensions ($10 \times 10^6$ cells/ml) were incubated with the fluorescent probe Fura-2/acetoxymethyl ester (Molecular Probe, Eugene, Oreg.) (1 μM for 30 min at 37° C.). The cells were then washed free of the extracellular probe and resuspended in Hank's balanced salt solution (HBSS) containing 1.6 mM calcium and supplemented with 10 mM HEPES. Suspensions of Fura-2-loaded cells were treated with EBV ($10^6$ transforming units [TFU]/ml) and with IL-8 or Groα(100 nM) in different sequences. Fluorescence (FIGS. 2a, 2b and 2c) was monitored (excitation and emission wavelengths, 340 and 510 nm, respectively) using an Aminco-Bowman, series 2 Apparatus (SLM-Aminco, Rochester, N.Y.). Viral preparations of EBV strain B95-8 were produced as previously described. Briefly, B95-8, which were mycoplasma-free tested, were grown in RPMI 1640 medium supplemented with 10% heat-inactivated FBS. When the viability of the cells were found to be less than 20%, cell-free culture supernatants were harvested and filtered through a 0.45 mm pore size filter, and the viral particles were further purified by ultracentrifugation. The virus pellet was suspended in 5 mM sodium phosphate (pH 7.5) and purified by centrifugation on a 10 to 30% (wt/vol) dextran gradient. Concentrated viral preparations were resuspended in RPMI 1640, aliquoted and stored at −80° C. until used. Viral titers were found to be $1 \times 10^7$ transforming units (TFU)/ml. The results shown in FIGS. 2a, 2b and 2c are further explained below:

FIG. 2a: a: Groα(100 nM); b: EBV; c: IL-8 (100 nM)

FIG. 2b: a: Groα(100 nM); b: IL-8 (100 nM); c: EBV

FIG. 2c: a: EBV ⅒ dilution, $10^5$ TFU/ml; b: EBV; c: Groα(100 nM); d: IL-8 (100 nM).

EXAMPLE 3
Effect of Pertussis Toxin on the $Ca^{2+}$ Mobilization and De Novo RNA Synthesis Induced by EBV in Human Neutrophils Human neutrophils ($10 \times 10^6$ cells/ml) were preincubated 2 hours at 37° C. in the presence of 0.5 mg/ml of pertussis toxin (which catalyzes the ADP-ribosylation of G-protein and inhibits G-protein-mediated events) during two hours, prior to EBV ($10^6$ TFU/ml) or IL-8 (100 nM) stimulation. Calcium mobilization was measured as described in Example 2. Results are set out in FIG. 3a in which:

a: stimulation with IL-8;

b: stimulation with EBV;

c: pretreatment with pertussis toxin and stimulation with IL-8;

d: pretreatment with pertussis toxin and stimulation with EBV.

EBV-induced RNA synthesis was studied by measurement of the incorporation of [5-$^3$H] uridine into total RNA. Neutrophils (5×10$^6$ cells/ml) pretreated or not with pertussis toxin (0.5 mg/ml) were suspended in HBSS buffer supplemented with 1% heat-inactivated (1 h, 56° C.) autologous plasma. One hundred ml aliquotes of the cell suspensions were incubated in 96-well microtiter plates in the presence of 1 mCi of [5-$^3$H] uridine (per sample) and treated with 3 nM of GM-CSF (positive control) or with infectious EBV (10$^6$ TFU/ml). Plates were incubated during five hours at 37° C. under a humid atmosphere containing 5% $CO_2$. Following this incubation period, cells were harvested by filtration through glass fiber discs and radioactivity was measured in a liquid scintillation counter. Pertussis toxin was obtained from Sigma Chemicals (St. Louis, Mo.) and used in solution in NaCl 0.9% containing 0.01% BSA. Groα was obtained from Peprotech and used as described above for pertussis toxin.

Figure 3B:
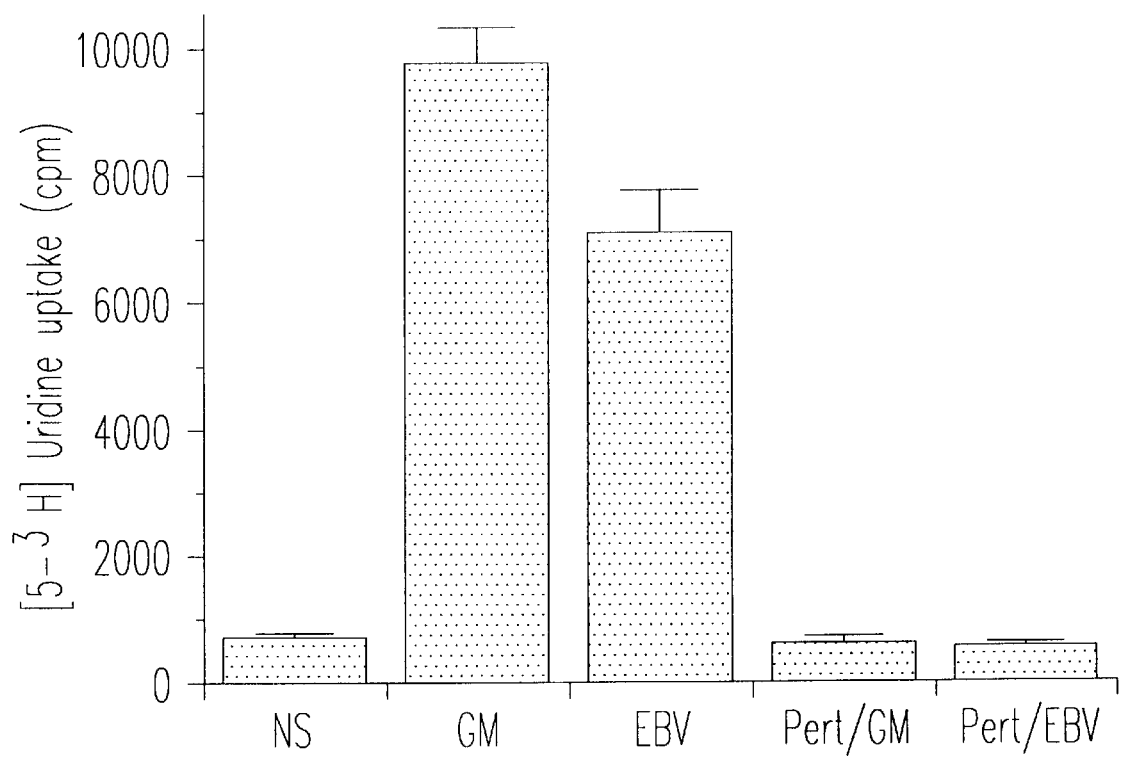

The results illustrated in FIG. 3b are representative of six different experiments (GM-CSF, granulocyte-macrophage colony-stimulating factor).

We claim:

1. A method for the treatment of a viral infection in a human or animal comprising administering to a human or animal in need of such treatment, a pharmacologically acceptable, therapeutically effective amount of an interleukin-8 agent, wherein said viral infection is of a DNA virus selected from the group consisting of parvoviridae, papovaviridae, adenoviridae, herpesviridae, poxviridae and hepadnaviridae; with the proviso that IL-8 agent excludes peptides of about 17 amino acids having the following formula:

$$\text{Glu-Leu-Arg-Cys-Xaa}_1\text{-Cys Xaa}_2\text{-Xaa}_3\text{-Xaa}_{4\text{-}Xaa5}\text{-Xaa}_6\text{-Xaa}_7\text{-Xaa}_8\text{-Xaa}_9\text{-Xaa}_{10}\text{-Xaa}_{11}\text{-Xaa}_{12}$$

wherein:

$Xaa_1$ is Gln, Met, or Val;

$Xaa_2$ is Ile, or Val;

$Xaa_3$ is Lys, Gln, or Ser;

$Xaa_4$ is Thr, or Ile;

$Xaa_5$ is Tyr, Leu, Met, His, Val, or Thr;

$Xaa_6$ is Ser, Gln, Thr, or Ala;

$Xaa_7$ is Lys, Arg, or His;

$Xaa_8$ is absent or is Pro, Phe, or Gly;

$Xaa_9$ is absent or is Phe, Ile, or Val;

$Xaa_{10}$ is absent or is His, Lys, or Arg;

$Xaa_{11}$ is absent or is Pro, Leu, or Phe; and $Xaa_{12}$ is absent or is Lys, His or Arg.

2. A method according to claim 1 wherein said agent is interleukin-8 protein or an analog thereof which elicits an interleukin-8 biological response.

3. A method for the treatment of a viral infection in a human or animal comprising administering to a human or animal in need of such treatment, a pharmacologically acceptable, therapeutically effective amount of an interleukin-8 agent, wherein said viral infection is of an RNA virus selected from the group consisting of picornaviridae, togaviridae, orthomyxoviridae, paramyxoviridae, coronaviridae, reoviridae, oncornaviridae and filoviridae;

with the proviso that IL-8 agent exclude peptides of about 17 amino acids having the following formula:

$$\text{Glu-Leu-Arg-Cys-Xaa}_1\text{-Cys Xaa}_2\text{-Xaa}_3\text{-Xaa}_4\text{-Xaa}_5\text{-Xaa}_6\text{-Xaa}_7\text{-Xaa}_8\text{-Xaa}_9\text{-Xaa}_{10}\text{-Xaa}_{11}\text{-Xaa}_{12}$$

wherein:

$Xaa_1$ is Gln, Met, or Val;

$Xaa_2$ is Ile, or Val;

$Xaa_3$ is Lys, Gln, or Ser;

$Xaa_4$ is Thr, or Ile;

$Xaa_5$ is Tyr, Leu, Met, His, Val, or Thr;

$Xaa_6$ is Ser, Gln, Thr, or Ala;

$Xaa_7$ is Lys, Arg, or His;

$Xaa_8$ is absent or is Pro, Phe, or Gly;

$Xaa_9$ is absent or is Phe, Ile, or Val;

$Xaa_{10}$ is absent or is His, Lys, or Arg;

$Xaa_{11}$ is absent or is Pro, Leu, or Phe; and $Xaa_{12}$ is absent of is Lys, His or Arg.

4. A method according to claim 1 wherein said agent is interleukin-8 protein of 79 amino acids.

5. A method according to claim 1 wherein said agent is interleukin-8 protein of 72 amino acids.

6. A method according to claim 1 wherein said viral infection is of herpesviridae selected from the group consisting of EBV, HSV-1, HSV-2, CMV, VZV, HHV-6, HHV-7 and HHV-8.

7. A method according to claim 3, wherein said viral infection is of togaviridae which is a bovine diarrhea virus.

8. A method according to claim 3, wherein said viral infection is of picornaviridae which is a porcine enterovirus.

9. A method according to claim 3, wherein said viral infection is of paramyxoviridae or bovine respiratory syncytial virus.

10. A method according to claim 1 wherein said agent is administered in conjunction with an antiviral agent selected from the group consisting of interferon -α, -β, -γ, tumor necrosis factor-α, ganciclovir, acyclovir, vidarabine, idoxuridine, prostaglandins and prostaglandin analogs.

11. A method according to claim 1 wherein said human or animal is an immunosuppreased patient or animal, or a patient treated with a drug known to enhance the occurrence of viral infections.

12. A method according to claim 11, wherein said drug is selected from the group consisting of azathioprine, corticosteroids, adriamyicine and methotrexate.

13. A method for the treatment of cancer caused by oncoviruses in a human or animal comprising administering to a human or animal in need of such treatment, a pharmacologically acceptable, therapeutically effective amount of interleukin-8 agent.

14. A method according to claim 13 wherein said agent is administered in combination with an anticancer agent selected from the group consisting of adriamycine, cyclophosphamide and methotrexate.

15. An antiviral pharmaceutical formulation comprising a pharmacologically acceptable, therapeutically effective amount of an interleukin-8 agent, in association with a pharmaceutically acceptable carrier.

* * * * *